US 6,420,186 B1

(12) United States Patent
Berger et al.

(10) Patent No.: US 6,420,186 B1
(45) Date of Patent: Jul. 16, 2002

(54) METHOD FOR DEPOSITING A FLATTENED DROPLET ON A SURFACE AND APPARATUS THEREFOR, AND A PUMP THEREFOR

(75) Inventors: Abraham Berger, Givataim; Ben Zion Haim, Holon; Baruch Meirovich, Hod Hasharon; Avri Hazan, Givataim, all of (IL)

(73) Assignee: A.R.T. Medical Instruments Ltd., Hod Hasharon (IL)

( * ) Notice: Subject to any disclaimer, the term of this patent is extended or adjusted under 35 U.S.C. 154(b) by 0 days.

(21) Appl. No.: 09/529,065

(22) PCT Filed: Oct. 14, 1998

(86) PCT No.: PCT/IL98/00498

§ 371 (c)(1),
(2), (4) Date: Jul. 5, 2000

(87) PCT Pub. No.: WO99/18872

PCT Pub. Date: Apr. 22, 1999

(30) Foreign Application Priority Data

Oct. 14, 1997 (IL) .................................................. 121968

(51) Int. Cl.[7] .......................... G01N 1/10; G01N 35/08; G01N 33/48; G01N 21/00; G01N 1/14; C12M 1/36; C12M 1/38; B01L 3/02; B67D 5/00; B67D 5/40

(52) U.S. Cl. .......................... 436/180; 436/54; 436/63; 436/65; 422/100; 422/67; 435/286.4; 73/863.71; 73/864; 73/864.01; 73/864.11; 73/864.15; 73/864.34; 222/3; 222/372; 222/385

(58) Field of Search .................. 422/63, 68.1, 100, 422/67; 436/180, 63, 54, 65; 73/863.71, 864, 864.01, 864.11, 864.15, 864.34; 222/3, 372, 385; 435/309.1, 286.4

(56) References Cited

U.S. PATENT DOCUMENTS

| 3,982,899 | A | | 9/1976 | Kelm .......................... 23/259 |
|---|---|---|---|---|
| 4,971,763 | A | * | 11/1990 | Columbus |
| 4,988,481 | A | | 1/1991 | Jarvimaki et al. .......... 422/100 |
| 5,204,268 | A | * | 4/1993 | Matsumoto |
| 5,496,272 | A | | 3/1996 | Kelm .......................... 23/259 |
| 5,593,893 | A | * | 1/1997 | Kobashi et al. |
| 5,629,201 | A | * | 5/1997 | Nugteren et al. |
| 5,707,588 | A | * | 1/1998 | Tsukishima |
| 5,785,926 | A | * | 7/1998 | Seubert et al. |
| 5,879,944 | A | * | 3/1999 | Komatsu |
| 5,916,524 | A | * | 6/1999 | Tisone |
| 5,927,547 | A | * | 7/1999 | Papen et al. |
| 6,033,911 | A | * | 3/2000 | Schultz et al. |
| 6,063,339 | A | * | 5/2000 | Tisone et al. |
| 6,079,283 | A | * | 6/2000 | Papen et al. |
| 6,220,075 | B1 | * | 4/2001 | Papen et al. |
| 6,269,846 | B1 | * | 8/2001 | Overbeck et al. |
| 6,133,045 | A1 | * | 10/2001 | Johnson et al. |
| 2001/0039053 | A1 | * | 11/2001 | Liseco et al. |

FOREIGN PATENT DOCUMENTS

DE         89 09 141 U         8/1990

\* cited by examiner

Primary Examiner—Jill Warden
Assistant Examiner—Brian R. Gordon
(74) Attorney, Agent, or Firm—Nath & Associates PLLC; Gary M. Nath; Marvin C. Berkowitz

(57) ABSTRACT

A method and apparatus is provided for depositing a flattened droplet on a surface. The method includes the steps of providing a tube with a distal end that contains a microvolume of liquid, issuing an outgoing flow of displacement gas for slowly discharging substantially the entire microvolume of liquid as a droplet on the surface, and controllably blowing one or more bubbles into the droplet for flattening the droplet on the surface.

9 Claims, 5 Drawing Sheets

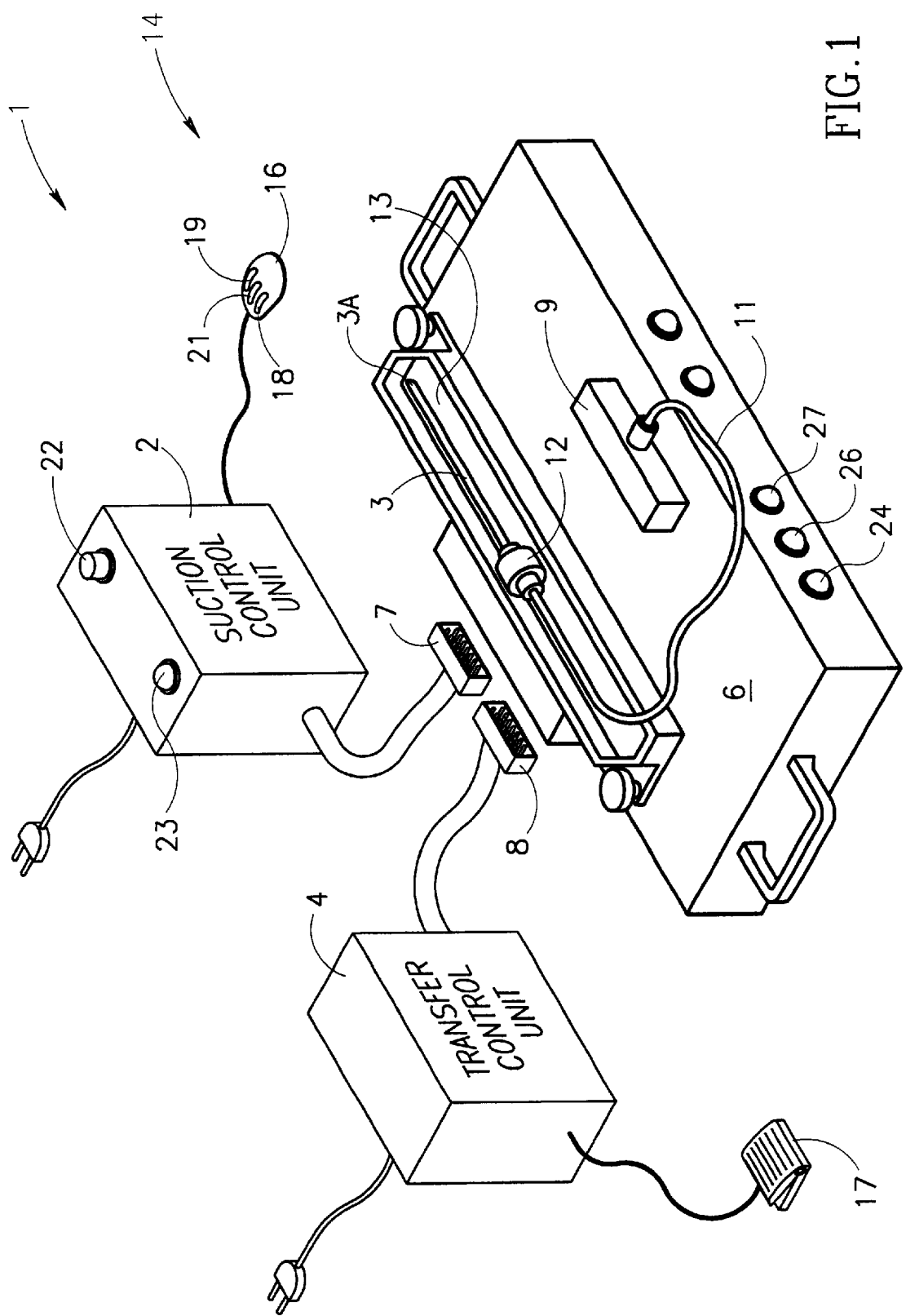

METHOD FOR DEPOSITING A FLATTENED DROPLET ON A SURFACE AND APPARATUS THEREFOR, AND A PUMP THEREFOR

FIELD OF THE INVENTION

The invention relates to a method for depositing a flattened droplet on a surface suitable for in vitro fertilization (IVF) and embryo transfer (ET), and apparatus therefore, and a pump therefor.

BACKGROUND OF THE INVENTION

In an IVF-ET procedure, oocytes are aspirated from female ovaries and inseminated in vitro with male sperm in a culture medium to form embryos which are incubated prior to their being transferred to a subject by means of a two-stage transfer procedure. The transfer procedure includes the aspiration of a relatively large volume of about 20–40 µl of culture medium containing between one to five embryos into a transfer catheter by means of a manually operated syringe and its subsequent injection into a subject.

Since a conventional IVF-ET procedure is manual, the rate of injection of the embryo containing culture into a uterine cavity may vary significantly. Thus, on the one hand, too slow an injection rate may cause embryo containing culture medium to trickle down the transfer catheter's outer surface and, on the other hand, too quick an injection rate may severely damage embryo(s) following their collision against a uterine wall. The latter case may also flood a subject's uterus possibly resulting in a failed procedure as embryos are either washed out of her uterus or implanted in one of her Fallopian tubes leading to an ectopic pregnancy. Another disadvantage attendant with the use of a relatively large volume of culture medium is that it may alter the specific properties of the micro-environment within a subject's uterus required for successful embryo implantation and its normal development.

The present invention is based on the notion that substantially automating embryo implantation in IVF-ET procedures may overcome some of the shortcomings of the conventional IVF-ET procedure.

SUMMARY OF THE INVENTION

In accordance with the present invention, there is provided a method for depositing a flattened droplet on a surface particularly suitable for depositing embryo(s) containing culture medium at a desired site in a uterus cavity, and apparatus therefor, and a pump therefor.

In accordance with a first aspect of the invention, there is provided a method for depositing a flattened droplet on a partially absorbent surface, the method comprising the steps of:

(a) providing a narrow bore transfer tube having a proximal end and a distal end and containing a microvolume of liquid, the proximal end connected to a pneumatic system for issuing an outgoing flow of displacement gas into the transfer tube and drawing an incoming flow of displacement gas thereinto from the transfer tube; and (b) issuing an outgoing flow of displacement gas for slowly discharging substantially the entire microvolume of liquid as a droplet on the surface-and controllably blowing one or more bubbles into the droplet towards the end of its discharge to flatten the droplet on the surface.

A "flattened droplet" in the context of the present invention can be demonstrated on standard 80 gram/m$^2$ A4 paper for use with ink jet printers, such paper constituting a partially absorbent surface on which a flattened droplet of the present invention has a projected surface area about three to six times larger than that of a naturally forming dome-like droplet. A "partially absorbent surface" in the context of the present invention is one which absorbs a relatively insignificant volume of a naturally forming dome-like droplet over about 60 seconds. The flattening of a droplet as achieved by the method of the present invention is not by the relatively slow process of its being absorbed assuming it does not dry but rather as a consequence of its being effectively inflated by one or more bubbles of displacement gas controllably blown thereinto towards the end of its discharge which typically occurs over 5–20 seconds from an initial outward displacement of the microvolume of liquid. The surface may be flat, inclined or even inverted and still maintain the droplet in its flattened shape by virtue of the prevailing surface tension therewith.

A "microvolume of liquid" in the context of the present invention is a volume of liquid in the microliter range, e.g., within the range of 0.05–5 µl, preferably within the range of 0.1–3.0 µl, and particularly within the range of 0.3–2.0 µl. In the case of an IVF-ET procedure on a human subject when the catheter is upwardly inclined, even though the discharge of culture medium is relatively slow, its volume is so small so as to avoid a downward trickle along the catheter's outer surface.

In accordance with a preferred embodiment of the present invention, step (a) includes:

(a1) preventing capillary forces to draw liquid into the transfer tube upon insertion of its distal end into a vessel containing liquid;

(a2) inserting the transfer tube's distal end into the liquid;

(a3) drawing an incoming flow of displacement gas from the transfer tube such that a microvolume of liquid is drawn thereinto; and (a4) removing the transfer tube's distal end from the liquid.

The step of preventing capillary forces is preferably achieved by issuing an outgoing flow of displacement gas into the transfer tube so as to create a positive pressure therein. Alternatively, this step can be achieved, for example, by providing a seal at its distal end. After the transfer tube's distal end is removed from the liquid, the microvolume of liquid is preferably inwardly drawn away from its distal end as a safety precaution whereafter the inward displacement is neutralized by a brief outgoing flow of displacement gas into the transfer tube.

After the discharge of the microvolume of liquid from the transfer tube, the flattened droplet in most cases is still connected to the transfer tube's distal end and therefore to prevent its suction back into the transfer tube, the outgoing flow of displacement gas is maintained until the droplet is disconnected from the transfer tube's distal end by manually withdrawing the transfer tube. This outgoing flow of displacement gas may also remove any small quantities of the microvolume which were not initially discharged and which may include an embryo(s) in an IVF-ET procedure.

In accordance with a second aspect of the present invention, there is provided apparatus for depositing a flattened droplet of liquid on a partially absorbent surface, the apparatus for use with a narrow bore transfer tube having a proximal end and a distal end and a vessel of liquid, the apparatus comprising:

(a) a pneumatic system connected to the transfer tube's proximal end and adapted for issuing an outgoing flow of displacement gas into said transfer tube and drawing an incoming flow of displacement gas thereinto from said transfer tube; and (b) a control mechanism for controlling said pneumatic system in different operational modes including:

a user controlled suction mode for drawing an incoming flow of displacement gas from the transfer tube whereby a microvolume of liquid is drawn thereinto prior to the removal of said distal end from the vessel; and a user initiated automated delivery mode for issuing an outgoing flow of displacement gas into the transfer tube for slowly discharging substantially the entire microvolume of liquid as a droplet on the surface and controllably blowing one or more bubbles into the droplet towards the end of its discharge to flatten the droplet on the surface.

In accordance with a third aspect of the present invention, there is provided a pump comprising a housing having a bore with an internal peripheral surface, and a stationary annular sealing member integrally formed therewith at a first end of a pair of opposite ends; a slide rod disposed in said bore and having an external peripheral surface and a displacement annular sealing member integrally formed therewith; said sealing members sealing said peripheral surfaces to define a vented displacement volume therebetween whose volume is proportional to an annular cross section area between said peripheral surfaces and a distance between said sealing members; and said slide rod being slidably reciprocable between first and second positions respectively toward and away from said stationary sealing member whereupon said displaceable sealing member moves to reduce said volume to issue an outgoing flow of displacement gas from said displacement volume on a downstroke of said slide rod from said second position to said first position and said displaceable sealing member moves to increase said volume to draw an incoming flow of displacement gas into said displacement volume on an upstroke of said slide rod from said first position to said second position.

Preferably both the bore and the slide rod are of a right cylindrical shape such that the displacement volume has a cross sectional area defined by $\pi(a^2-a^2)$ where a and b are the radii of the bore's internal peripheral surface and the slide rod's external peripheral surface, respectively. Preferably, the cross section area is in the order of 4–10 mm$^2$ and the pump has a displacement volume incrementally changeable in the order of 0.1–0.4 µl.

BRIEF DESCRIPTION OF THE DRAWINGS

In order to understand the invention and how it is used, a preferred embodiment will now be described by way of a non-limiting example only, with reference to the accompanying drawings in which:

FIG. 1 is a pictorial view of apparatus for depositing a flattened droplet on a surface in accordance with the present invention;

FIGS. 2A–2L illustrates operation of the apparatus of FIG. 1 for depositing the flattened droplet on the surface;

DETAILED DESCRIPTION OF THE DRAWINGS

Figure 2A:
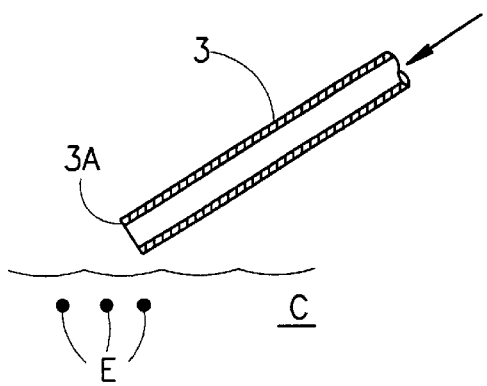
Figure 2B:
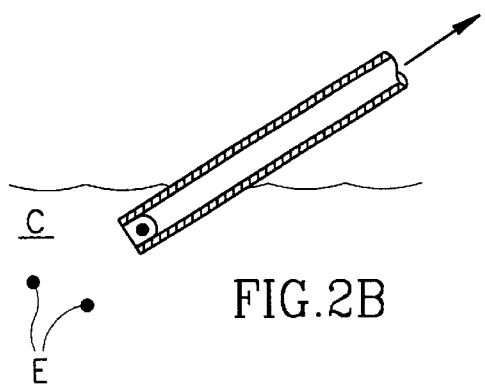

With reference now to FIGS. 1 and 2, apparatus 1 is employed for depositing a flattened droplet F on a partially absorbent surface S, for example, on a subject's endometrium in an IVF-ET procedure. Apparatus 1 includes a suction control unit 2 normally permanent located in a laboratory for the preparation of an embryo carrying catheter 3 constituting a transfer tube, a transfer control unit 4 normally permanently located in treatment room where an IVF-ET procedure is carried out and a portable casing 6 for consecutive connection to the suction control unit 2 and the transfer control unit 4 by means of connectors 7 and 8. The casing 6 includes a pneumatic system 9 which is permanently connected to the catheter 3 during an entire IVF-ET procedure via suitable air tubing 11 and an air filter 12. The casing 6 also has a receptacle 13 for accommodating the catheter 3 during its transport from the laboratory to the treatment room.

The pneumatic system 9 is under a control mechanism 14 including a computer mouse 16 for controlling the suction control unit 2 for initiating a user controlled suction mode to prepare the catheter 3 with a microvolume of embryo containing culture medium and a foot pedal 17 for controlling the transfer control unit 4 for initiating a user initiated automated delivery mode for depositing the flattened droplet F on the surface S. The computer mouse 16 has an upstroke control 18 for drawing an incoming flow of displacement gas into the pneumatic system 9 from the catheter 3, a downstroke control 19 for issuing an outgoing flow of displacement gas from the pneumatic system 9 into the catheter 3 and optionally a speed control 21 for controlling he flow rate of the displacement gas either from or into the pneumatic system 9. The suction control unit 2 is also provided with a reset button 22 for priming the pneumatic system 9 for a pre-suction mode of issuing an outgoing flow of displacement gas as indicated by a READY indicator light 23 prior to the preparation of the catheter 3. The different stages of the automatic delivery mode are indicated by a READY indicator light 24, a GO indicator light 26 and a DONE indicator light 27.

In operation, the casing 6 is initially connected to the suction control unit 2 and the catheter 3 is connected to the pneumatic system 9 via the air tubing 11 and the filter 12. An operator presses the reset button 22 whereupon a lit READY indicator light 23 indicates an outgoing flow of displacement gas creating a positive pressure within catheter 3 to prevent capillary forces drawing culture medium thereinto upon insertion of its distal end 3A into a vessel of culture medium C containing embryos E shown exaggerated in all FIGS. 2A–2L (see FIG. 2A). The operator inserts the distal end 3A into the vessel of culture medium C for aspirating about 0.3 to 0.6 µl microvolume of culture medium containing an embryo E into the catheter 3 (see FIG. 2B). Once an embryo is clearly seen to be close to the catheter's distal end 3A, the rate of aspiration of culture medium may be increased by depressing the speed control 21. IF a single embryo is to be transferred, distal end 3A is then be removed from the culture medium otherwise additional embryos may be captured as shown.

Figure 2C:
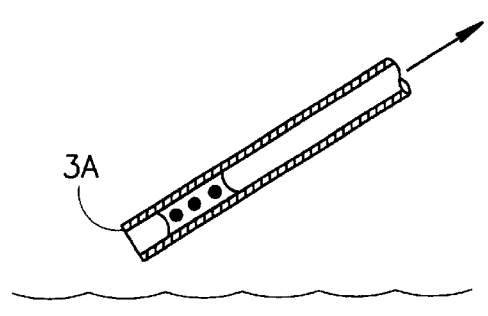
Figure 2D:
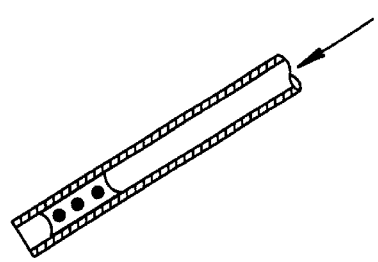
Figure 2E:
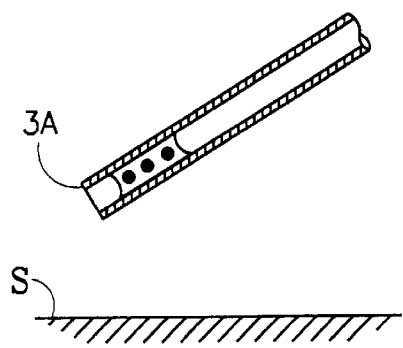
Figure 2F:
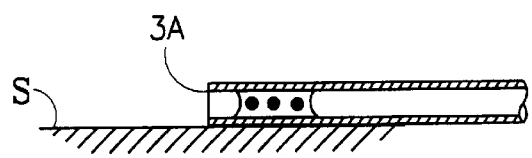
Figure 2G:
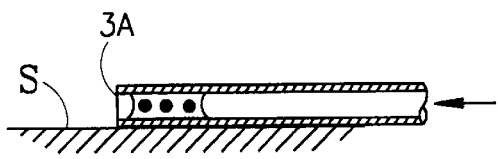
Figure 2H:
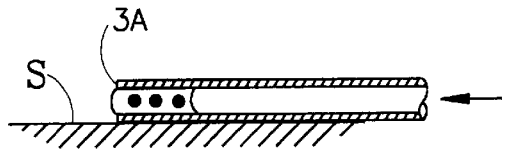
Figure 2J:
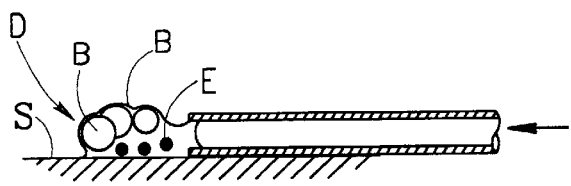
Figure 2K:
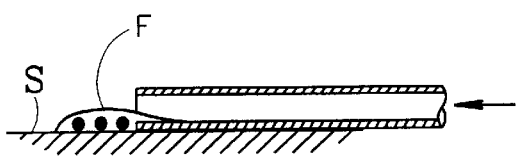

Once the catheter 3 contains one or more embryos, the operator withdraws its distal end 3A from the culture medium and the proceeds to depress the downstroke control 19 to slowly displace the microvolume of culture medium inwardly (see FIG. 2C). After the microvolume of culture medium has been inwardly displaced by about 5–15 mm from the catheter's distal end 3A, its motion is arrested by a momentary outgoing flow of displacement gas (see FIG. 2D) so that it finally comes to rest at a distance of about 10 mm (see FIG. 2E) therefrom thereby ensuring that it cannot be inadvertently lost during transportation of the casing 6 between the laboratory and the treatment room. The catheter 3 is then placed in the receptacle 13 (see FIG. 1) during the transportation of the casing 6 from the laboratory to the treatment room.

For transfer of the embryos E onto the surface S, the catheter 3 is laid on the surface S (see FIG. 2F) whereupon a first depression on the foot pedal 17 causes the READY indicator light 24 to be lit indicating that the automatic delivery mode can be initiated. Thereafter, a second depression on the foot pedal 17 causes the GO indicator light 26 to be lit indicating that an outgoing flow of displacement gas is displacing the microvolume of culture medium towards the catheter's distal end 3A (see FIG. 2G). The outgoing flow of displacement gas causes a concave shaped meniscus to be slowly formed which increases in size until it suddenly ruptures whereby most of the microvolume of culture medium is discharged as a droplet D on the surface S (see FIGS. 2H and 2J). The discharge is accompanied by one or more air bubbles B for effectively inflating the droplet D thereby considerably widening its projected surface area on the surface S to form the flattened droplet F whose shape is maintained by its prevailing surface tension with the surface S (see FIG. 2K).

Figure 2L:
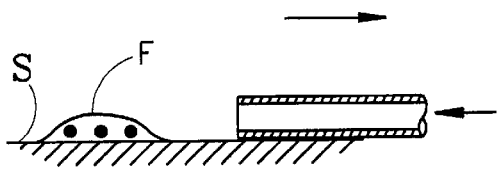

The GO indicator light 26 is then extinguished indicating that the operator should slightly withdraw the catheter 3 so as to detach it from the droplet F whilst at the same time there is an outgoing flow of displacement gas (see FIG. 2L). In the case of an actual IVF-ET procedure, withdrawal is limited to between about 10–15 mm such that the catheter's distal end 3A still lies along a subject's endometrium. Finally, a further outgoing flow of additional displacement gas is provided so as to remove any culture medium which may remain in the catheter 3. The DONE indicator light 27 is then lit to indicate that the catheter 3 can be completely removed.

Figure 3:
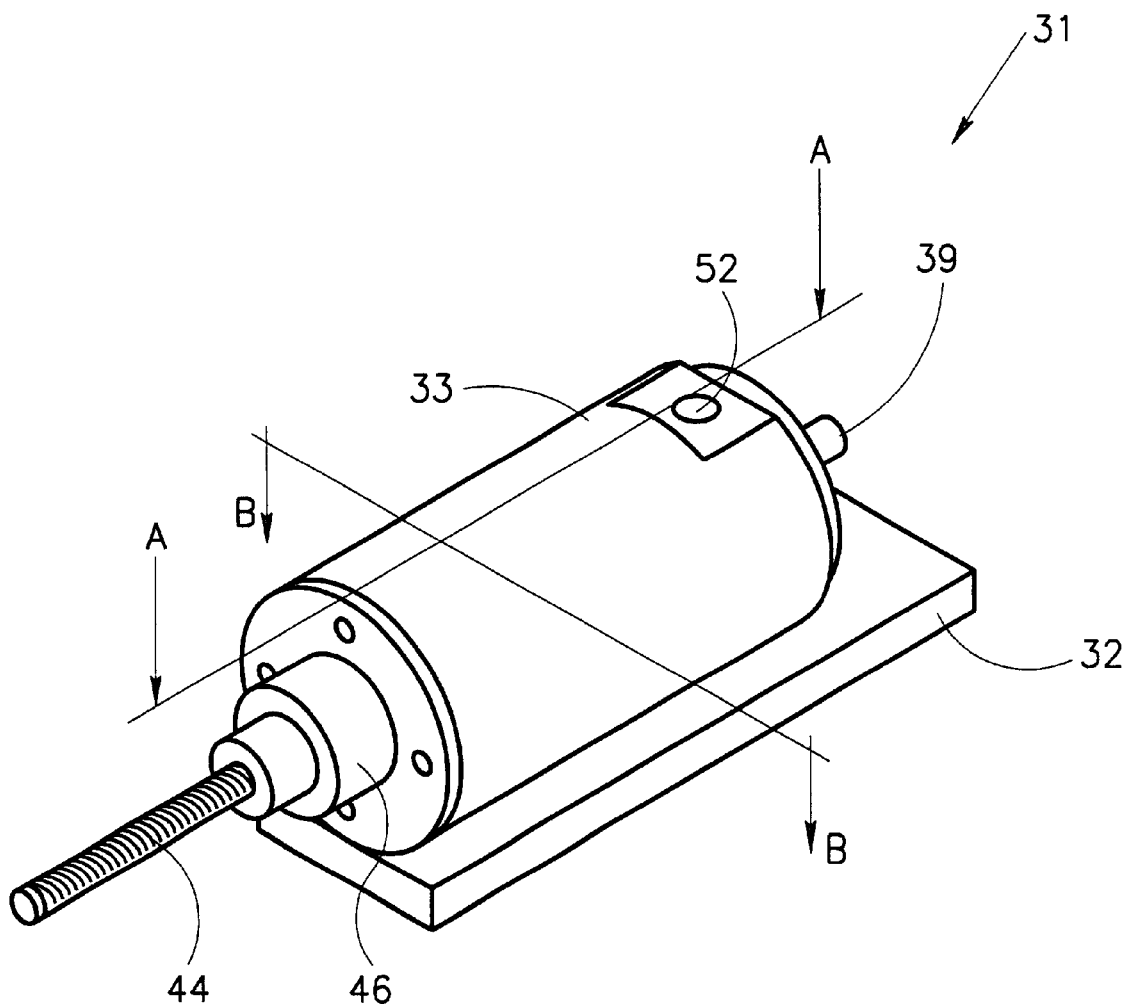
FIG. 3 is a pictorial view of a pump in accordance with the present invention.
Figure 4:
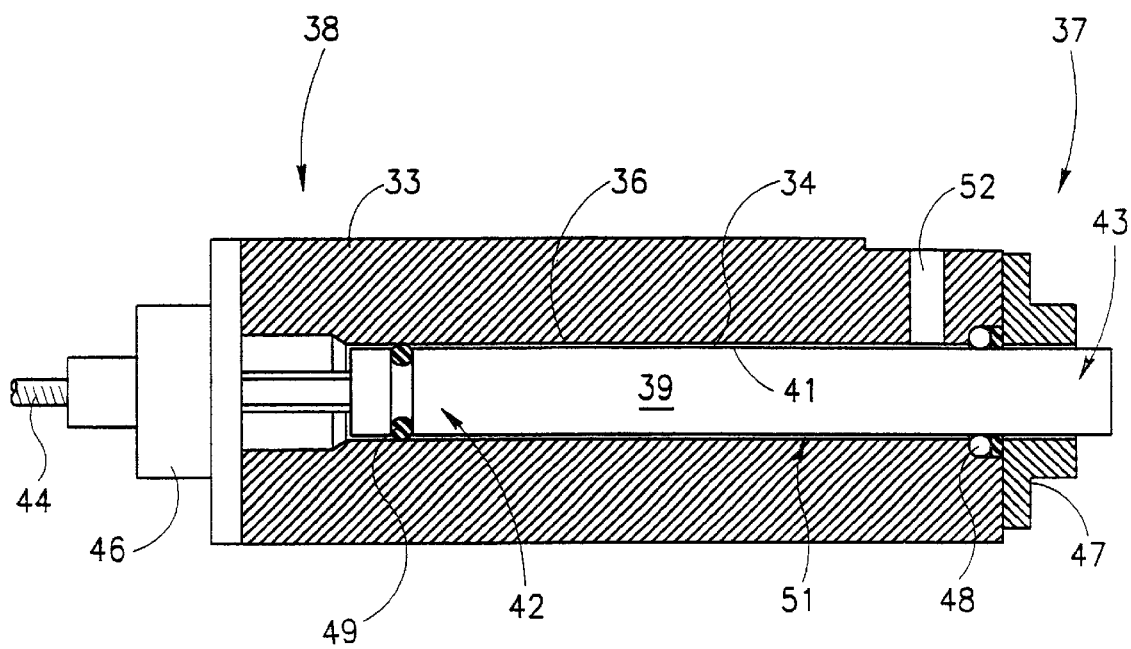
FIGS. 4 and 5 are cross sectional views of the pump of FIG. 3 along lines A—A and B—B in FIG. 3, respectively.
Figure 5:
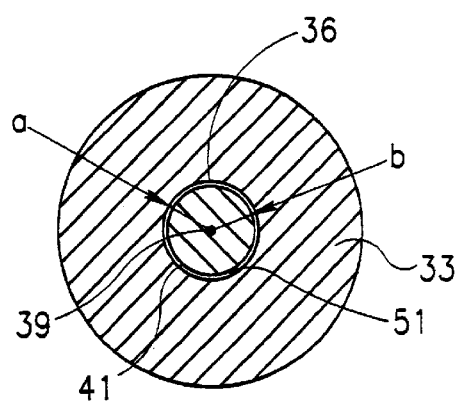

With reference now to FIGS. 3–5, a pump 31 constituting a pneumatic system for use with the apparatus 1 includes a base 32 with a housing 33 having a longitudinal right cylindrical throughbore 34 with an internal peripheral surface 36 of a radius a and having first and second opposite ends 37 and 38. A right cylindrical slide rod 39 with an external peripheral surface 41 of a radius b and first and second opposite end 42 and 43 is disposed in the bore 34 and is slidingly reciprocated by means of a linear actuator screw 44 driven by a step motor 46.

A sleeve bearing 47 having a sealing O-ring gasket 48 constituting a stationary annular sealing member is disposed at the first end 37 and an O-ring gasket 49 constituting a displaceable annular sealing member is disposed at the slide rod end 42, the gaskets 48 and 49 sealingly the peripheral surfaces 36 and 41 to define a displacement volume 51 vented by a vent 52. The displacement volume 51 has a volume equal to a product of a cross sectional area between the surfaces 36 and 41 defined by $\pi(a^2-b^2)$ and the distance between the gaskets 48 and 19.

The slide rod 39 is slidingly reciprocable between first and second positions respectively toward and away from the gasket 48 whereupon the displacement volume 51 has a minimum value when the gaskets 48 and 49 are adjacent in which case a major portion of the slide rod 39 is exterior to the bore 34 and a maximum value when the gaskets 48 and 49 are remote from one another. In operation, the gasket 49 moves to reduce the volume of the displacement volume 51 to issue an outgoing flow of displacement gas therefrom on a downstroke of the slide rod 39 from its second position to its first position and the gasket 49 moves to increase the volume of the displacement volume 51 to draw an incoming flow of displacement gas thereinto on an upstroke of the slide rod 39 from its first position to its second position.

The bore 34 and the slide rod 39 typically have diameters in the range of about 5–10 mm and which differ in the range of about 0.3–0.7 mm such that the cross section area is in the order of about 4–10 mm$^2$. The threading on actuator screw 44 is designed such that each step of the motor 46 causes an incremental movement of the slide rod 39 of about 0.001–0.002 inches. The motor 46 is typically driven at a rate of about 20–300 steps per second.

Various modifications and changes may be made in the configuration described above that come within the spirit of the invention. The invention enbraces all such changes and modifications coming within the scope of the appended claims.

What is claimed is:

1. A method for depositing a flattened droplet on a partially absorbent surface comprising the steps of:
   (a) providing a narrow bore transfer tube having a proximal end and a distal end and containing a microvolume of liquid, the proximal end connected to a pneumatic system adapted for issuing an outgoing flow of displacement gas into the tube and drawing an incoming flow of displacement gas therefrom; and
   (b) issuing an outgoing flow of displacement gas for slowly discharging substantially the entire microvolume of liquid as a droplet on the surface and controllably blowing one or more bubbles into the droplet towards the end of its discharge for flattening the droplet on the surface.

2. The method of claim 1 wherein step (a) includes:
   (a1) preventing capillary forces from drawing liquid into the transfer tube upon the insertion of its distal end into a vessel containing liquid;
   (a2) inserting the transfer tube's distal end into the vessel;
   (a3) drawing an incoming flow of displacement gas from the transfer tube such that a microvolume of liquid is drawn thereinto; and
   (a4) removing the transfer tube's distal end from the liquid.

3. The method of claim 2 wherein step (a1) includes issuing an outgoing flow of displacement gas into the transfer tube.

4. The method of claim 3 further comprising the step of:
   (a5) drawing the microvolume of liquid into the transfer tube away from its distal end; and
   (a6) neutralizing the inward displacement by a brief outgoing flow of displacement gas into the transfer tube.

5. The method according to claim 1 further comprising the step of:
   (c) providing an additional outflow of displacement gas while displacing the transfer tube away from the droplet so separate the droplet from its distal end.

6. The method according to claim 1 wherein the microvolume of liquid is a culture medium containing embryo(s) which are urged against the surface by the droplet's prevailing surface tension.

7. Apparatus for depositing a flattened droplet on a partially absorbent surface, the apparatus for use with a narrow bore transfer tube having a proximal end and a distal end and a vessel of liquid, the apparatus comprising:
   (a) a pneumatic system connected to the transfer tube's proximal end and adapted for issuing an outgoing flow of displacement gas into said transfer tube and drawing an incoming flow of displacement gas thereinto from said transfer tube; and (b) a control mechanism for controlling said pneumatic system in different operational modes including:

an user controlled suction mode for drawing an incoming flow of displacement gas from said transfer tube whereby a microvolume of liquid is drawn thereinto prior to the removal of said distal end from the vessel; and an user initiated automated delivery mode for issuing an outgoing flow of displacement gas into said transfer tube for slowly discharging substantially the entire microvolume of liquid as a droplet on the surface and controllably blowing one or more bubbles into the droplet towards the end of its discharge for flattening the droplet on the surface.

8. Apparatus according to claim 7 wherein said control mechanism includes an automatic pre-suction mode for issuing an outgoing flow of displacement gas.

9. Apparatus according to claim 1 claim 7 wherein separate units house a suction control unit for controlling said user controlled suction mode and a transfer control unit for controlling said user initiated automatic delivery mode.

* * * * *

UNITED STATES PATENT AND TRADEMARK OFFICE
CERTIFICATE OF CORRECTION

PATENT NO.    : 6,420,186 B1
DATED         : July 16, 2002
INVENTOR(S)   : Abraham Berger et al.

It is certified that error appears in the above-identified patent and that said Letters Patent is hereby corrected as shown below:

Column 6,
Line 58, change "so" to -- to --.

Column 8,
Line 8, delete "claim 1".

Signed and Sealed this

Fifth Day of November, 2002

Attest:

Attesting Officer

JAMES E. ROGAN
Director of the United States Patent and Trademark Office